(12) United States Patent
Hoernig et al.

(10) Patent No.: US 11,653,887 B2
(45) Date of Patent: May 23, 2023

(54) METHOD FOR CREATING A SYNTHETIC MAMMOGRAM ON THE BASIS OF A DUAL ENERGY TOMOSYNTHESIS RECORDING

(71) Applicant: Siemens Healthcare GmbH, Erlangen (DE)

(72) Inventors: Mathias Hoernig, Moehrendorf (DE); Steffen Kappler, Effeltrich (DE); Julia Wicklein, Neunkirchen a. Br. (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 308 days.

(21) Appl. No.: 17/029,182

(22) Filed: Sep. 23, 2020

(65) Prior Publication Data
US 2021/0093275 A1 Apr. 1, 2021

(30) Foreign Application Priority Data

Sep. 30, 2019 (EP) .................................... 19200330

(51) Int. Cl.
*A61B 6/00* (2006.01)
*A61B 6/02* (2006.01)

(52) U.S. Cl.
CPC .............. *A61B 6/502* (2013.01); *A61B 6/025* (2013.01); *A61B 6/4021* (2013.01);
(Continued)

(58) Field of Classification Search
CPC ......... A61B 6/025; A61B 6/482; A61B 6/502; A61B 6/5223
See application file for complete search history.

(56) References Cited

U.S. PATENT DOCUMENTS 9,808,215 B2 11/2017 Ruth et al.
10,010,302 B2 7/2018 Ruth et al.
(Continued)

FOREIGN PATENT DOCUMENTS

EP 3326535 A1 5/2018

OTHER PUBLICATIONS

Huang, Hailiang et al. "Comparison of contrast-enhanced digital mammography and contrast-enhanced digital breast tomosynthesis for lesion assessment" Journal of Medical Imaging. Vol. 6; No. 03; 2019 // ISSN: 2329-4302; DOI: 10.1117/1.JMI.6.3.031407.
(Continued)

*Primary Examiner* — Dani Fox
(74) *Attorney, Agent, or Firm* — Harness, Dickey & Pierce, P.L.C.

(57) ABSTRACT

A method is for creating a synthetic mammogram based upon a dual energy tomosynthesis recording of an examination region. In an embodiment the method includes making a low energy tomosynthesis recording with a first X-ray energy spectrum; making a high energy tomosynthesis recording with a second X-ray energy spectrum of relatively higher energy compared with the first X-ray energy spectrum, wherein the examination region includes a contrast medium distribution; determining a subtraction volume based upon the high energy tomosynthesis recording and the low energy tomosynthesis recording; generating a three-dimensional probability map with a weighting factor per voxel based upon the subtraction volume; and creating a synthetic mammogram based upon the three-dimensional probability map.

20 Claims, 3 Drawing Sheets

(52) U.S. Cl.
CPC ............ *A61B 6/4035* (2013.01); *A61B 6/481* (2013.01); *A61B 6/482* (2013.01); *A61B 6/5235* (2013.01); *A61B 6/54* (2013.01)

(56) References Cited

U.S. PATENT DOCUMENTS

| | | |
|---|---|---|
| 2014/0072096 A1 | 3/2014 | Hoernig |
| 2017/0011534 A1 | 1/2017 | Costa |
| 2018/0000430 A1* | 1/2018 | Hoernig ............... A61B 6/4241 |
| 2018/0158228 A1 | 6/2018 | Karssemeijer et al. |

OTHER PUBLICATIONS

Van Schie, Guido et al. "Generating Synthetic Mammograms From Reconstructed Tomosynthesis Volumes" IEEE Transactions on Medical Imaging: vol. 32; No. 12; pp. 2322-2331; Dec. 2013 // DOI:10.1109/tmi.2013.2281738.

* cited by examiner

METHOD FOR CREATING A SYNTHETIC MAMMOGRAM ON THE BASIS OF A DUAL ENERGY TOMOSYNTHESIS RECORDING

PRIORITY STATEMENT

The present application hereby claims priority under 35 U.S.C. § 119 to European patent application number EP 19200330.9 filed Sep. 30, 2019, the entire contents of which are hereby incorporated herein by reference.

FIELD

Embodiments of the invention generally relate to a method for creating a synthetic mammogram based upon a dual energy tomosynthesis recording of an examination region and also a mammography system, which enable a calculation of a synthetic mammogram with a reduced superposition of tumor-laden regions.

BACKGROUND

Contrast medium-enhanced dual energy mammography of the breast (CEDEM—Contrast Enhanced Dual Energy Mammography, CEDM—Contrast Enhanced Digital Mammography) is a method in X-ray diagnostics in which high-energy (HE) X-ray images/recordings are created after contrast medium administration and low energy (LE) images/recordings are subtracted from them with weighting but without contrast medium administration. The aim is the improved detectability of lesions due to the contrast medium accumulation within the blood vessels feeding the tumors. From dual energy imaging in digital mammography (DM) using iodine as the contrast medium, also known as the dual spectrum method, an improved diagnosis is expected by the radiologist as well as an improvement in the sensitivity and specificity. CEDEM can be carried out, for example, in the form of a so-called titanium contrast-enhanced mammography.

The adaptation of the above method from 2D to 3D is known as CEDET (Contrast-Enhanced Dual Energy Tomosynthesis). Hereby, two tomosynthesis scans are recorded with different X-ray spectra or different X-ray tube voltages, in which similarly to CEDEM, the representation of an iodine contrast medium accumulation takes place. The resulting subtraction volume based upon the two tomosynthesis scans corresponds to a 3D map or a 3D distribution of regions relevant to the tumor. In the context of digital tomosynthesis recording (Digital Breast Tomosynthesis, DBT), typically, in addition to the (three-dimensional) slice images, a synthetic mammogram is calculated which corresponds to a two-dimensional recording of the existing data set and is reconstructed from the slices.

From the publication U.S. Pat. No. 9,808,215 B2, for example, a method for calculating a synthetic mammogram is known. A 2D mammogram image is thereby synthesized from at least one image data set reconstructed from tomosynthesis projection images and/or from the tomosynthesis. In the simplest form, the mammography can be synthesized by selection of one of the tomosynthesis projection images for representation as a synthesized mammography. Other methods for the synthesis of a mammography involve the new projection and filtration of projection data and/or reconstructed data. The synthesized mammography is displayed together with at least one part of the reconstructed data to facilitate the checking of the reconstructed data. A trusted image is generated which can be used to facilitate the checking of a tomosynthesis data set.

In a typical calculation of a synthetic mammogram based upon an average intensity projection (AIP) and a maximum intensity projection (MIP), based upon the tomosynthesis slices, not all the tumor-relevant regions are represented sufficiently clearly. For example, the superposition of dense tissue can result in the loss of visibility of the structures bordering a tumor, for example, so-called spiculi and the margins. However, the representation of such structures is particularly relevant and interesting for the diagnosis, since it facilitates the identification of a tumor for the diagnosing radiologist and represents an indicator of the malignancy of the tumor.

In conventional tomosynthesis, for example, in the context of a screening, CAD methods based upon artificial intelligence (AI) are utilized for identifying lesions within the 3D slices. From the publication EP 3 326 535 A1, there is known, for example, a display system for the display of data of digital breast tomosynthesis (DBT). First and second DBT volume images of the left breast of a woman and first and second DBT volume images of the right breast of the woman are provided by way of an image creation unit. Furthermore, for each DBT volume image, a two-dimensional navigation image is provided by a navigation image provision unit, whereby a user is permitted to specify a position in the navigation image using a user interface, whereupon a CAD marker assigned to the location is determined in a DBT volume image of a breast and a corresponding CAD marker, where present, is determined in another DBT volume image of the breast. Sections of this DBT volume image that are associated with the CAD markers are shown on a display. These CAD methods are based upon Deep Learning methods in which neural networks, such as the U-net, are trained with a plurality of data sets with known lesion positions, in particular with image annotations. Subsequently, the trained networks are capable of generating, on unknown data sets, a probability distribution of regions relevant to the tumor.

The so-called probability maps arising therefrom can subsequently be used to make the recognized regions in the synthetic two-dimensional image visible. During the creation, a different weighting of the individual slices takes place based upon the probability distributions or probability map and thus prevents or reduces interfering superpositions of regions laden with tumor. From the publication U.S. Pat. No. 10,010,302 B2, it is known that a 2D mammogram image is synthesized from at least one image data set reconstructed from tomosynthesis projection images and/or the tomosynthesis. In the simplest form, the mammography can be synthesized by selection of one of the tomosynthesis projection images for representation as a synthesized mammogram. Other methods for the synthesis of a mammogram involve the new projection and filtration of projection data and/or reconstructed data. The synthesized mammogram is displayed together with at least one part of the reconstructed data to facilitate the checking of the reconstructed data. Thus, a trusted image can be generated which can be used to facilitate the checking of a tomosynthesis data set.

SUMMARY

Embodiments of the invention are directed to a method for creating a synthetic mammogram, a mammography system, a computer program product and a computer-readable medium which enable a simplified and alternative calculation of a synthetic mammogram with a reduced superposition of tumor-laden regions.

Embodiments according to the invention are directed to a method for creating a synthetic mammogram based upon a dual energy tomosynthesis recording; a mammography system; a computer program product; and a computer-readable medium.

At least one embodiment of the invention relates to a method for creating a synthetic mammogram, in particular, with a reduced superposition of tumor-laden regions based upon a dual energy tomosynthesis recording of an examination region. The method includes recording a low energy tomosynthesis recording; recording a high energy tomosynthesis recording; determining; generating; creating and display. In the making a low energy tomosynthesis recording, a low energy tomosynthesis recording is made with a first X-ray energy spectrum. In the making a high energy tomosynthesis recording, a high energy tomosynthesis recording is made with a second X-ray energy spectrum of higher energy compared with the first X-ray energy spectrum, whereby the examination region has a contrast medium distribution. In the determining, a subtraction volume is determined based upon the high energy tomosynthesis recording and the low energy tomosynthesis recording. In the generation, a three-dimensional probability map is generated with a weighting factor per voxel based upon the subtraction volume. In the creation, a synthetic mammogram is created based upon the three-dimensional probability map and, in particular the low energy tomosynthesis recording. The synthetic mammogram can be designated a contrast-enhanced synthetic mammogram.

At least one embodiment of the invention further relates to a mammography system having way for carrying out a method according to at least one embodiment of the invention. The advantages of the method according to at least one embodiment of the invention can advantageously be transferred to the mammography system.

The mammography system of at least one embodiment can comprise the following units:

a recording unit for making a low energy tomosynthesis recording with a first X-ray energy spectrum and for making a high energy tomosynthesis recording with a second X-ray energy spectrum of higher energy compared with the first X-ray energy spectrum, whereby the examination region has a contrast medium distribution, a determining unit for determining a subtraction volume based upon the high energy tomosynthesis recording and the low energy tomosynthesis recording, a generating unit for generating a three-dimensional probability map with a weighting factor per voxel based upon the subtraction volume, a creating unit for creating a synthetic mammogram based upon the three-dimensional probability map, and a display unit, for example, in the form of a screen, for displaying the synthetic mammogram.

At least one embodiment of the invention further relates to a computer program product with a computer program which can be loaded directly into a memory store of a control apparatus of a mammography system, having program portions in order to carry out all the steps of a method according to an embodiment of the invention when the computer program is executed in the control device of the mammography system.

At least one embodiment of the invention further relates to a computer-readable medium on which program portions that are configured to be read in and executed by a computer unit are stored, in order to carry out all the steps of a method according to an embodiment of the invention when the program portions are executed by the mammography system or its computer unit.

At least one embodiment is directed to a method for creating a synthetic mammogram based upon a dual energy tomosynthesis recording of an examination region, the method comprising:

making a low energy tomosynthesis recording with a first X-ray energy spectrum;

making a high energy tomosynthesis recording with a second X-ray energy spectrum of relatively higher energy compared with the first X-ray energy spectrum, wherein the examination region includes a contrast medium distribution;

determining a subtraction volume based upon the high energy tomosynthesis recording and the low energy tomosynthesis recording;

generating a three-dimensional probability map with a weighting factor per voxel based upon the subtraction volume; and creating a synthetic mammogram based upon the three-dimensional probability map.

At least one embodiment is directed to a mammography system, comprising:

a control apparatus configured for creating a synthetic mammogram based upon a dual energy tomosynthesis recording of an examination region, the at least one processor being configured for:

making a low energy tomosynthesis recording with a first X-ray energy spectrum;

making a high energy tomosynthesis recording with a second X-ray energy spectrum of relatively higher energy compared with the first X-ray energy spectrum, wherein the examination region includes a contrast medium distribution;

determining a subtraction volume based upon the high energy tomosynthesis recording and the low energy tomosynthesis recording;

generating a three-dimensional probability map with a weighting factor per voxel based upon the subtraction volume; and creating a synthetic mammogram based upon the three-dimensional probability map.

At least one embodiment is directed to a non-transitory computer program product storing a computer program, directly loadable into a memory store of a control apparatus of a mammography system, including program sections to carry out the method of an embodiment when the computer program is executed in the control apparatus of the mammography system.

At least one embodiment is directed to a non-transitory computer-readable medium storing program portions, configured to be read in and executed by a computer unit, to carry out the method of an embodiment when the program portions are executed by the mammography system.

BRIEF DESCRIPTION OF THE DRAWINGS

Example embodiments of the invention will now be described in more detail, making reference to the drawings. In the drawings.

DETAILED DESCRIPTION OF THE EXAMPLE EMBODIMENTS

Figure 1:
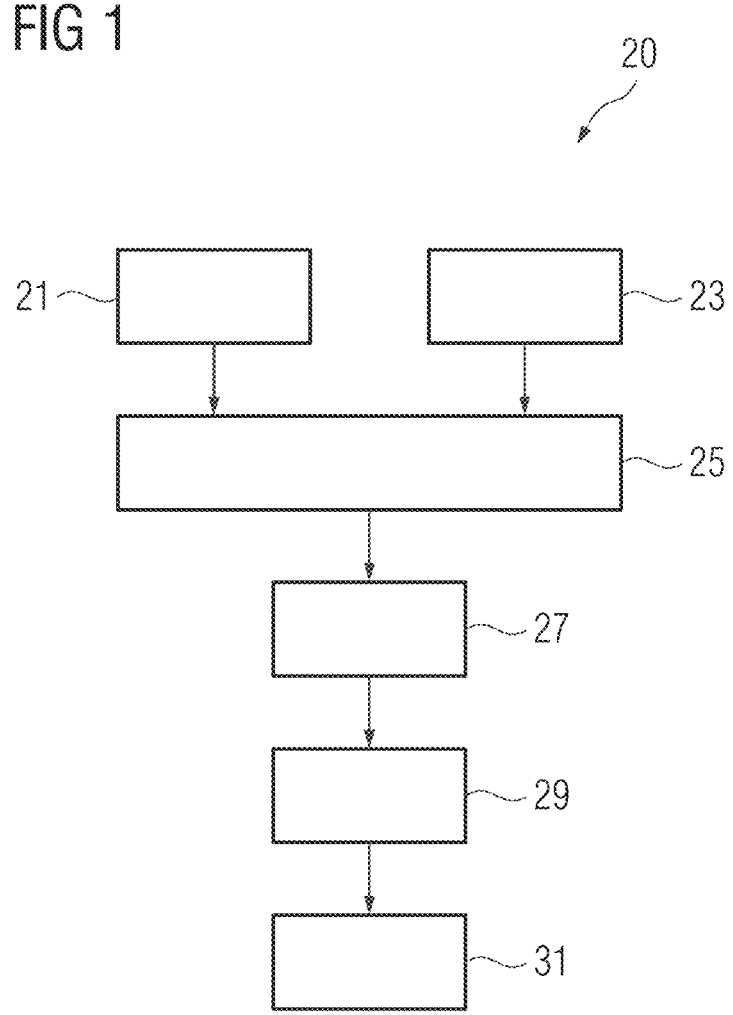
FIG. 1 is a schematic representation of the method according to an embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for creating a synthetic mammogram, in particular, with a reduced superposition of tumor-laden regions based upon a dual energy tomosynthesis recording of an examination region. The method includes recording a low energy tomosynthesis recording; recording a high energy tomosynthesis recording; determining; generating; creating and display. In the making a low energy tomosynthesis recording, a low energy tomosynthesis recording is made with a first X-ray energy spectrum. In the making a high energy tomosynthesis recording, a high energy tomosynthesis recording is made with a second X-ray energy spectrum of higher energy compared with the first X-ray energy spectrum, whereby the examination region has a contrast medium distribution. In the determining, a subtraction volume is determined based upon the high energy tomosynthesis recording and the low energy tomosynthesis recording. In the generation, a three-dimensional probability map is generated with a weighting factor per voxel based upon the subtraction volume. In the creation, a synthetic mammogram is created based upon the three-dimensional probability map and, in particular the low energy tomosynthesis recording. The synthetic mammogram can be designated a contrast-enhanced synthetic mammogram.

For the preparation of the recording, a contrast medium is administered to the patient. During any waiting time, for example, of between 1.5 and 2 minutes, the contrast medium begins to be distributed, in particular, in the examination region. The patient can now be positioned and the breast compressed. Next, a low energy tomosynthesis recording can be made, for example, with a tungsten anode and a rhodium filter at a tube voltage of between 24 and 32 kV. In the low energy tomosynthesis recording, the contrast medium is already at least partially distributed in the tissue, although the influence of the contrast medium on the low energy tomosynthesis recording is small. Subsequently, the high energy tomosynthesis recording can be made, for example, with a titanium filter and a tube voltage of, for example, 49 kV. In the high energy tomosynthesis recording, the contrast medium is distributed in the tissue and the influence of the contrast medium on the high energy tomosynthesis recording is clearly recognizable.

The high energy tomosynthesis recording is made once a contrast medium has been introduced into the examination region. During the high energy tomosynthesis recording, a contrast medium accumulation, in particular, an iodine accumulation, takes place in the examination region. During the low energy tomosynthesis recording, however, a contrast medium accumulation or no contrast medium accumulation can be present in the examination region. Typically, in particular, in order to increase the level of patient comfort, both in the low energy tomosynthesis recording and in the high energy tomosynthesis recording, the contrast medium accumulation can be present. During the recording of the low energy tomosynthesis recording, the examination region can have a contrast medium distribution. The high energy tomosynthesis recording and the low energy tomosynthesis recording each comprise a data set with a plurality of projection data sets recorded at a plurality of projection angles. Proceeding therefrom, a tomosynthesis volume can be reconstructed for the high energy tomosynthesis recording and for the low energy tomosynthesis recording, respectively.

During creation, in particular, different weightings of the individual slices or voxels can be undertaken based upon probability distributions of the three-dimensional probability map. In particular, the low energy tomosynthesis recording can be combined with the three-dimensional probability map to a contrast-enhanced synthetic mammogram.

The subtraction volume can be calculated based upon the reconstructed tomosynthesis volume of the high energy tomosynthesis recording and the low energy tomosynthesis recording. Thereby, the image values of respective corresponding voxels of the tomosynthesis volume of the high energy tomosynthesis recording (HE) and of the tomosynthesis volume of the low energy tomosynthesis recording (LE) are subtracted in a weighted manner. For example, the subtraction can be carried out according to the following equation:

$$\ln(x)=\ln(HE)-w\cdot\ln(LE).$$

The factor w can be selected dependent upon the breast thickness/density, for example, based upon the compression thickness. The weighting factor of the three-dimensional probability map can be based upon the value x. The value range of the weighting factors of the three-dimensional probability map can extend, preferably, from 0 to 200 or from 0 to 2. The weighting factor specifies a probability or a weight for a voxel. The weighting factor of the three-dimensional probability map can comprise a contrast medium concentration which can be determined based upon the value x. Alternatively, the weighting factor can assume discrete values, for example 0 for a background, 1 for breast tissue and 2 for a lesion.

The three-dimensional probability map is generated in the step of generation based upon the subtraction volume. The weighting factors of the three-dimensional probability map can be a measure for the contrast medium concentration, in particular, iodine concentration.

The inventors propose a new alternative approach for a probability map for the case of a contrast medium-enhanced tomosynthesis recording. In place of a method based upon deep learning with corresponding training data, the probability map is based, according to the invention, upon the 3D map or 3D distribution of the subtraction volume obtained by way of the iodine accumulation. The strength of the accumulated iodine proportion corresponds to the probability or the degree of the malignancy of the lesion based upon its one iodine accumulation level.

In one embodiment, the data of a quantitative analysis of the iodine concentration from CEDET data (in mg iodine/cm$^3$) can be used for this. Subsequently, a superposition-free or at least superposition-reduced representation of the regions within the synthetic mammogram that are relevant, in particular, for the diagnosis can also take place.

In a contrast medium-enhanced breast tomosynthesis, the corresponding already existing contrast medium image, in particular, the iodine image or subtraction image can advantageously also be used to create a three-dimensional probability map. Advantageously, laborious collection of annotated data for a CAD-based method can be avoided. The collection of annotated data would be necessary for an approach using neural networks. Since the contrast medium-enhanced dual energy tomosynthesis recording represents a new type of X-ray diagnosis for tumor identification, currently no adequate database is available to access. The output quality of such trained networks depends, however, largely on the number and quality of the annotated training data. Advantageously, a more easily available method for calculating a three-dimensional probability map can be enabled for the contrast medium-enhanced dual energy tomosynthesis recording.

According to one embodiment of the invention, in the step of creating, a first synthetic mammogram is generated based upon the low energy tomosynthesis recording. The first synthetic mammogram can be created based upon a low energy tomosynthesis recording, for example, by way of known methods for creating synthetic mammograms.

The first synthetic mammogram or a synthetic mammogram can, in general, comprise the following steps and, in particular, can be based on the low energy tomosynthesis recording with a plurality of projection data sets. Preferably, at least a (first) synthetic mammogram according to the central projection data set, in particular, at a projection angle of 0°, is created. The central projection angle can thereby denote, in particular, the angle at which the central beam of the X-ray source falls substantially perpendicularly to the compressed breast or perpendicularly to the upper compression element. A (first) synthetic mammogram can be assigned to a projection angle in each case. For a projection angle, a (first) synthetic mammogram can be created. The (first) synthetic mammogram can be based, in particular, on the projection recording of the associated projection angle, for example, making use of this projection recording in the form of an average intensity projection.

In one embodiment, a plurality of (first) synthetic mammograms can be created. The maximum number of the created (first) synthetic mammograms can correspond, for example, to the number of projection angles. Preferably, a (first) synthetic mammogram is created for the projection angle 0°. Furthermore, two up to a maximum number of the recorded projection angles, preferably 10 to 20, particularly preferably 17 (first) synthetic mammograms are created. For example, 17 (first) synthetic mammograms are created based upon 25 projection data sets.

An average intensity projection (AIP) can be determined as the first image component based upon the plurality of projection data sets. Preferably, a projection data set of a projection angle can be used, in particular, according to the assignment of a projection angle to the (first) synthetic mammogram as an average intensity projection or as the basis for the average intensity projection. In particular, a limited-angle-AIP (LARIP) can be used as an average intensity projection. One projection data set or a plurality of projection data sets can be selected, based upon which the average intensity projection is determined. Advantageously, the average intensity projection comprises, as the first image component, essential information concerning the examination object in the two-dimensional plan view according to the projection angle. However, the average intensity projection alone can barely meet the requirements for a comprehensive assessment of the breast, since due to the merely proportionately used dose, it has a relatively high level of noise.

At least one of the following steps can be applied to the average intensity projection: intensity matching, grey value distribution matching, beam scatter correction and calcium-containing noise filters. The average intensity projection can be processed such that the processed average intensity projection can be used as a noisy basis or a first image component for the (first) synthetic mammogram. Advantageously, the information of this projection can serve as the basis for the (first) synthetic mammogram. Building upon the first image component, by adding edge information and contrast information of a second image component, a (first) synthetic mammogram that is substantially qualitatively equivalent to a conventional digital full field mammogram recording can be created.

A maximum intensity projection (MIP) based upon the plurality of projection data sets can be determined as the second image component. In particular, a plurality of projection data sets can be used to determine the maximum intensity projection. In particular, projection data sets can be used which are adjacent to the (first) synthetic mammogram assigned to the projection data set or its projection angle. For example, projection data sets of a suitable angular region round the assigned projection angle can be used. In particular, all the projection data sets can be used to determine the maximum intensity projection. Advantageously, edge information and contrast information from a plurality of projection data sets can be used as second image components in order to add them to the first image component.

Advantageously, the second image component can be used for noise removal.

From the tomosynthesis volume of the low energy tomosynthesis recording, a weighted intensity projection on the basis, for example, of the three-dimensional probability map, instead of an MIP, can alternatively be used as the second image component.

The first image component and the second image component can be recombined to a (first) synthetic mammogram. By adding or recombining the first image component and the second image component, the (first) synthetic mammogram can be created. Advantageously, particular emphasis is placed thereon that the information of the associated projection data set in the form of the first image component is used together with additional information from a plurality of or further projection data sets in the form of the second image component. By this way, the information based upon the patient dose used can advantageously be used for the creation of the (first) synthetic mammogram.

According to one embodiment of the invention, in the step of creating, by way of forward projection of the three-dimensional probability map, a two-dimensional probability map is generated. The three-dimensional probability map with the weighting factors as values for the voxels of the three-dimensional probability map can be forward projected. A two-dimensional probability map is thereby created. The two-dimensional probability map can preferably have weighting factors in the value range between 0 and 2. The value 1 way no amplification. The value 0 way complete suppression. The value 2 way maximum amplification.

The forward projection of the three-dimensional probability map can advantageously be used for a synthetic, in particular, contrast-enhanced mammogram. The weighting factors in the two or three-dimensional probability map can be dependent upon the breast thickness or the tube voltage(s).

According to one embodiment of the invention, the synthetic mammogram is a superposition of the first synthetic mammogram with the two-dimensional probability map. In the synthetic mammogram, the two-dimensional probability map can be represented, for example, as a colored superposition. Advantageously, the region with, in particular, superposed tumor-laden regions can be emphasized. Advantageously, the diagnosis can be improved.

According to one embodiment of the invention, the synthetic mammogram is based upon a weighting of the first synthetic mammogram with the two-dimensional probability map. The first synthetic mammogram can be created based upon the average intensity projection and the maximum intensity projection. The first synthetic mammogram can be weighted with the two-dimensional probability map. Thereby, a weighted synthetic mammogram can be obtained.

The two-dimensional probability map, preferably with values between 0 and 2, can be combined with the first synthetic mammogram to a synthetic mammogram. The weighting factors can be applied pixel-wise to the image values of the first synthetic mammogram. Thereby, a weighting in the two-dimensional image space can be carried out. Advantageously, an optimized synthetic mammogram can be enabled. Advantageously, a reduced superposition of tumor-laden regions in the synthetic mammogram can be enabled. Advantageously, the superposition can take place by way of an evaluation only of the data associated with the examination or recording.

According to one embodiment of the invention, in the step of creating, the three-dimensional probability map is combined with the low energy tomosynthesis recording to a weighted low energy tomosynthesis recording and the weighted low energy tomosynthesis recording is forward projected. The voxels, in particular each voxel of the tomosynthesis volume based upon the low energy tomosynthesis recording can be multiplied by, or weighted with, the weighting factor or the probability factor of the three-dimensional probability map. The value range of the three-dimensional probability map can preferably correspond to the range between 0 and 2.

Advantageously, the weighting can be carried out in the three-dimensional image space. This weighted three-dimensional image information can be transferred into the two-dimensional image space by way of the forward projection.

According to one embodiment of the invention, the forward-projected weighted low energy tomosynthesis recording is displayed as a synthetic mammogram. According to one embodiment of the invention, the forward-projected weighted low energy tomosynthesis recording is the synthetic mammogram. Advantageously, a clear representation in the two-dimensional image space can be used for diagnosis, in particular, as a survey image.

According to one embodiment of the invention, the forward-projected weighted low energy tomosynthesis recording is combined with an average intensity projection to a synthetic mammogram. The average intensity projection can be, for example, an average projection, for example 0°, of the low energy tomosynthesis recording. The forward-projected weighted low energy tomosynthesis recording comprises a weighted intensity per pixel. Additionally, a so-called calcium maximum intensity projection can be taken into account in the combination to the synthetic mammogram. Advantageously, a weighted synthetic mammogram can be enabled. Advantageously, a weighting in the three-dimensional image space can lead to a particularly strong reduction of superpositions in the tumor-laden region.

According to one embodiment of the invention, the synthetic mammogram is a superposition of the forward-projected weighted low energy tomosynthesis recording with a first synthetic mammogram based upon the low energy tomosynthesis recording. In the synthetic mammogram, the two-dimensional forward-projected, weighted low energy tomosynthesis recording can be mapped as, for example, colored superpositions on the first synthetic mammogram.

Advantageously, regions with, in particular superposed, tumor-laden regions can be emphasized. Advantageously, the diagnosis can be improved. Advantageously, a typical first synthetic mammogram can be mapped with the superposition based upon the three-dimensional weighting.

According to one embodiment of the invention, the total of the weighting factors of the three-dimensional probability map is normalized to a predetermined value for slices contributing one pixel of the synthetic mammogram, in particular all slices. The normalization of voxels assigned to one another of the plurality of slices can be 1 or 100. The assigned voxels can be defined in such a way that these voxels contribute to a common pixel in the synthetic mammogram.

Advantageously, a uniform representation of different synthetic mammograms can be enabled, for example, based upon different examinations.

According to one embodiment of the invention, the weighting factors of the three-dimensional probability map are based upon a quantitative analysis of the contrast medium concentration. The contrast medium can, in particular, be iodine. The contrast medium concentration can be given in mg iodine/cm$^3$.

According to one embodiment of the invention, the three-dimensional probability map is displayed in a volume image, in particular in addition to the synthetic mammogram, based upon the low energy tomosynthesis recording and/or superposed on the high energy tomosynthesis recording. For example, a scrolling or leafing or movement of the view of the volume image in the form of the subtraction volume can be enabled. Preferably, a region of interest (ROI) can be selected and possibly marked in the synthetic mammogram. An automatic display of the volume image or of the corresponding slice of the volume image based upon the selection of the region of interest can take place.

Advantageously, the clarity of the two-dimensional synthetic mammogram can be combined with the depth resolution of the three-dimensional volume image. Advantageously, an improved diagnosis can be enabled.

At least one embodiment of the invention further relates to a mammography system having way for carrying out a method according to at least one embodiment of the invention. The advantages of the method according to at least one embodiment of the invention can advantageously be transferred to the mammography system.

The mammography system of at least one embodiment can comprise the following units:

a recording unit for making a low energy tomosynthesis recording with a first X-ray energy spectrum and for making a high energy tomosynthesis recording with a second X-ray energy spectrum of higher energy compared with the first X-ray energy spectrum, whereby the examination region has a contrast medium distribution, a determining unit for determining a subtraction volume based upon the high energy tomosynthesis recording and the low energy tomosynthesis recording, a generating unit for generating a three-dimensional probability map with a weighting factor per voxel based upon the subtraction volume, a creating unit for creating a synthetic mammogram based upon the three-dimensional probability map, and a display unit, for example, in the form of a screen, for displaying the synthetic mammogram.

The determining unit, the generating unit and the creating unit can be included in a computer unit of the mammography system. The recording unit can comprise, in particular, the X-ray source and the X-ray detector.

At least one embodiment of the invention further relates to a computer program product with a computer program which can be loaded directly into a memory store of a control apparatus of a mammography system, having program portions in order to carry out all the steps of a method according to an embodiment of the invention when the computer program is executed in the control device of the mammography system.

At least one embodiment of the invention further relates to a computer-readable medium on which program portions that are configured to be read in and executed by a computer unit are stored, in order to carry out all the steps of a method according to an embodiment of the invention when the program portions are executed by the mammography system or its computer unit.

FIG. 1 shows an example embodiment of the method 20 according to the invention for creating a synthetic mammogram based upon a dual energy tomosynthesis recording of an examination region. The method 20 has the following steps: in the step of recording 21, a low energy tomosynthesis recording is made with a first X-ray energy spectrum. In the step of recording 23, a high energy tomosynthesis recording is made with a second X-ray energy spectrum of higher energy compared with the first X-ray energy spectrum, whereby the examination region has a contrast medium distribution. In the step of determining 25, a subtraction volume is determined based upon the high energy tomosynthesis recording and the low energy tomosynthesis recording. In the step of generating 27, a three-dimensional probability map is generated with a weighting factor per voxel based upon the subtraction volume. In the step of creating 29, a synthetic mammogram is created based upon the three-dimensional probability map. A step of displaying 31 the synthetic mammogram can follow.

In the step of creating 29, a first synthetic mammogram can be generated based upon the low energy tomosynthesis recording. In the step of creating 29, furthermore, by way of a forward projection of the three-dimensional probability map, a two-dimensional probability map can be generated. The synthetic mammogram can be a superposition of the first synthetic mammogram with the two-dimensional probability map. Alternatively, the synthetic mammogram can be based upon a weighting of the first synthetic mammogram with the two-dimensional probability map.

In an alternative embodiment, in the step of creating 29, the three-dimensional probability map can be combined with the low energy tomosynthesis recording to a weighted low energy tomosynthesis recording and the weighted low energy tomosynthesis recording can be forward-projected. The forward-projected weighted low energy tomosynthesis recording can be the synthetic mammogram. Alternatively, the forward-projected weighted low energy tomosynthesis recording can be combined with an average intensity projection to the synthetic mammogram. Alternatively, the synthetic mammogram can be a superposition of the forward-projected weighted low energy tomosynthesis recording with a first synthetic mammogram based upon the low energy tomosynthesis recording.

In the step of displaying 31, the three-dimensional probability map can further be displayed superposed in a volume image, in particular, the subtraction volume image, based upon the low energy tomosynthesis recording and/or the high energy tomosynthesis recording.

Figure 2:
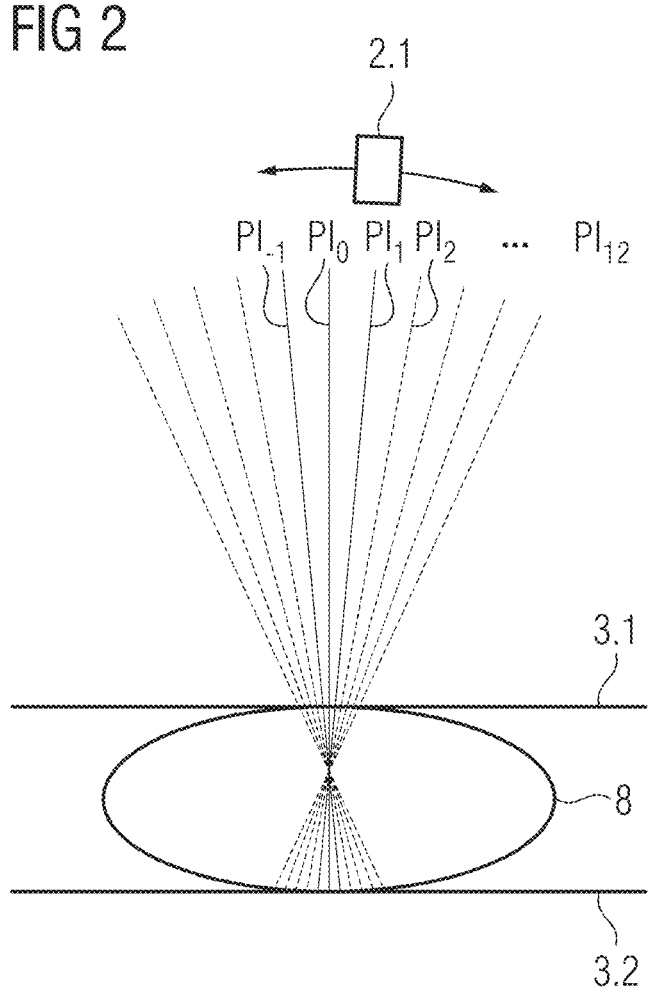
FIG. 2 is a schematic representation of the mammography system according to the invention in a first embodiment.

FIG. 2 shows an example embodiment of the mammography system according to the invention in a first embodiment. For a low energy tomosynthesis recording and a high energy tomosynthesis recording, respectively, a plurality of projection data sets is recorded at a plurality of projection angles PI-1, 0, 1, 2, . . . , 12. The X-ray source 2.1 is thereby moved, in particular, along a radius about a point in the breast 8, whereby a projection data set is recorded at each of the projection angles PI-1, 0, 1, 2, . . . , 12. During the recording, the breast 8 of a patient is arranged as the examination object between an upper compression element 3.1 and a lower compression element 3.2.

Figure 3:
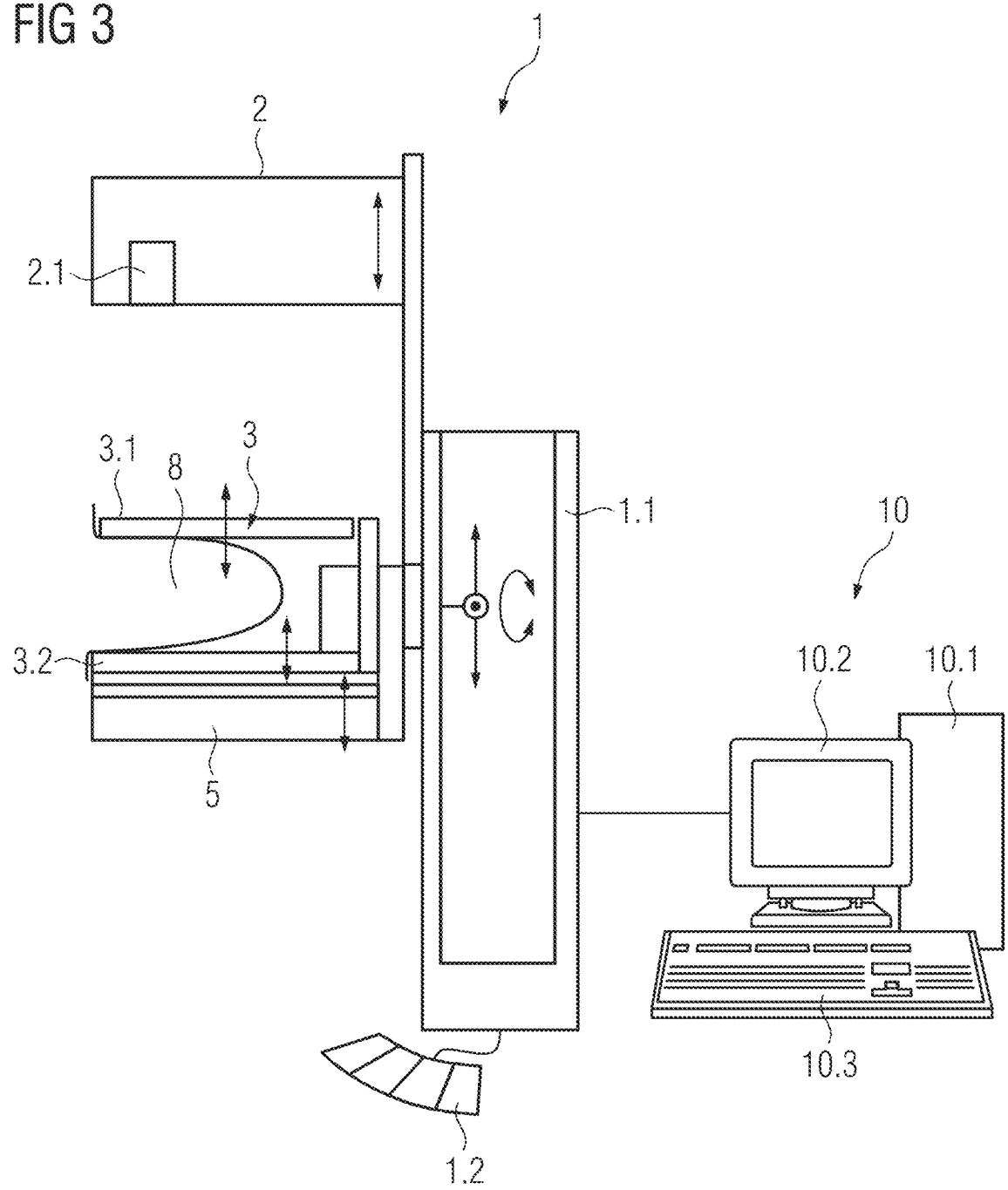
FIG. 3 is a schematic representation of the mammography system according to the invention in a second embodiment.

FIG. 3 shows an example embodiment of the mammography system 1 according to the invention in a second embodiment. The mammography system 1 comprises a stand 1.1 on which the X-ray housing 2 having the X-ray source 2.1 and the X-ray detector 5 are arranged together with a compression unit 3. In particular, the X-ray housing 2 is mounted on the stand 1.1 to be rotatable relative to the stand 1.1 and the X-ray detector 5 and the compression unit 3. The compression unit 3 includes an upper compression element 3.1 and a lower compression element 3.2, between which the breast 8 of a patient is arranged. The mammography system 1 is connected to a data processing unit 10. The data processing unit 10 comprises at least one processor unit or computer unit 10.1, a display unit 10.2 and an input unit 10.3. A marking of the region of interest can take place via the input unit. The computer unit 10.1 can comprise the determining unit, the generating unit and the creating unit. The mammography system 1 is at least partially controllable via a foot switch 1.2.

Although embodiments of the invention have been illustrated in detail with the preferred example embodiment, the invention is not restricted by the examples given and other variations can be derived therefrom by a person skilled in the art without departing from the protective scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a way-plus-function element within the meaning of 35 U.S.C. § 112(f) unless an element is expressly recited using the phrase "way for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for creating a synthetic mammogram based upon a dual energy tomosynthesis recording of an examination region, the method comprising:
    making a low energy tomosynthesis recording with a first X-ray energy spectrum;
    making a high energy tomosynthesis recording with a second X-ray energy spectrum of relatively higher energy compared with the first X-ray energy spectrum, wherein the examination region includes a contrast medium distribution;
    determining a subtraction volume based upon the high energy tomosynthesis recording and the low energy tomosynthesis recording;
    generating a three-dimensional probability map with a weighting factor per voxel based upon the subtraction volume; and
    creating a synthetic mammogram based upon the three-dimensional probability map.

2. The method of claim 1, wherein in the creating, a first synthetic mammogram is generated based upon the low energy tomosynthesis recording.

3. The method of claim 2, wherein in the creating, by way of forward projection of the three-dimensional probability map, a two-dimensional probability map is generated.

4. The method of claim 3, wherein the synthetic mammogram is a superposition of the first synthetic mammogram with the two-dimensional probability map.

5. The method of claim 3, wherein the synthetic mammogram is based upon a weighing of the first synthetic mammogram with the two-dimensional probability map.

6. The method of claim 2, wherein in the creating, the three-dimensional probability map is combined with the low energy tomosynthesis recording to a weighted low energy tomosynthesis recording and the weighted low energy tomosynthesis recording is forward projected.

7. The method of claim 6, wherein the forward-projected weighted low energy tomosynthesis recording is the synthetic mammogram.

8. The method of claim 6, wherein the forward-projected weighted low energy tomosynthesis recording is combined with an average intensity projection to the synthetic mammogram.

9. The method of claim 6, wherein the synthetic mammogram is a superposition of the forward-projected weighted low energy tomosynthesis recording with a first synthetic mammogram based upon the low energy tomosynthesis recording.

10. The method of claim 1, wherein the total of the weighting factors of the three-dimensional probability map is normalized to a value for slices contributing one pixel of the synthetic mammogram.

11. The method of claim 1, wherein the weighting factors of the three-dimensional probability map are based upon a quantitative analysis of the contrast medium concentration.

12. The method of claim 1, wherein the three-dimensional probability map is at least one of displayed in a volume image based upon the low energy tomosynthesis recording and superposed on the high energy tomosynthesis recording.

13. A mammography system, comprising:
    a control apparatus configured for creating a synthetic mammogram based upon a dual energy tomosynthesis recording of an examination region, the at least one processor being configured for:
    making a low energy tomosynthesis recording with a first X-ray energy spectrum;
    making a high energy tomosynthesis recording with a second X-ray energy spectrum of relatively higher energy compared with the first X-ray energy spectrum, wherein the examination region includes a contrast medium distribution;
    determining a subtraction volume based upon the high energy tomosynthesis recording and the low energy tomosynthesis recording;

generating a three-dimensional probability map with a weighting factor per voxel based upon the subtraction volume; and creating a synthetic mammogram based upon the three-dimensional probability map.

14. A non-transitory computer program product storing a computer program, directly loadable into a memory store of a control apparatus of a mammography system, including program sections to carry out the method of claim 1 when the computer program is executed in the control apparatus of the mammography system.

15. A non-transitory computer-readable medium storing program portions, configured to be read in and executed by a computer unit, to carry out the method of claim 1 when the program portions are executed by the mammography system.

16. The method of claim 1, wherein in the creating, the three-dimensional probability map is combined with the low energy tomosynthesis recording to a weighted low energy tomosynthesis recording and the weighted low energy tomosynthesis recording is forward projected.

17. The method of claim 16, wherein the forward-projected weighted low energy tomosynthesis recording is the synthetic mammogram.

18. The method of claim 16, wherein the forward-projected weighted low energy tomosynthesis recording is combined with an average intensity projection to the synthetic mammogram.

19. The method of claim 2, wherein the total of the weighting factors of the three-dimensional probability map is normalized to a value for slices contributing one pixel of the synthetic mammogram.

20. The method of claim 2, wherein the weighting factors of the three-dimensional probability map are based upon a quantitative analysis of the contrast medium concentration.

* * * * *